United States Patent [19]

Grolman

[11] 4,160,330
[45] Jul. 10, 1979

[54] APPARATUS AND METHOD FOR MAKING OPHTHALMIC MEASUREMENTS

[75] Inventor: Bernard Grolman, Worcester, Mass.

[73] Assignee: American Optical Corporation, Southbridge, Mass.

[21] Appl. No.: 881,093

[22] Filed: Feb. 24, 1978

[51] Int. Cl.² ............................................. A61B 3/10
[52] U.S. Cl. ......................................... 33/200; 351/5
[58] Field of Search .................. 33/200, 174 D; 351/5

[56] References Cited

U.S. PATENT DOCUMENTS 2,536,367  1/1951  Holmes ................................. 33/200

FOREIGN PATENT DOCUMENTS 201678  3/1939  Switzerland.

Primary Examiner—Richard E. Aegerter
Assistant Examiner—John W. Shepperd
Attorney, Agent, or Firm—Jeremiah J. Duggan; Alan H. Spencer

[57] ABSTRACT

A device for use in fitting lenses to spectacles frames wherewith ophthalmic measurements are applied directly to frames selected by patients. A frame without lenses is adjusted to fit the patient, the fitting device is applied to the frame and the whole placed upon the face. Measurements of distances from extreme lateral and inferior points on the frame rims to the patient's visual axis in the case of each eye are taken for use in edging the lenses to a size and shape which will locate their optical centers in coincidence with the patient's visual axes when the spectacles are glazed and put to use.

8 Claims, 5 Drawing Figures

APPARATUS AND METHOD FOR MAKING OPHTHALMIC MEASUREMENTS

BACKGROUND OF THE INVENTION

1. Field of the Invention

This invention relates to improvements in measuring apparatus and method for use in fitting ophthalmic lenses in spectacles frames.

2. Description of the Prior Art

Fitting lenses to spectacles frames requires, in each case of each lens, the taking of measurements which can be used to locate the lens optical center in proper relationship relative to the patient's visual axis when the spectacles are worn.

While various measuring scales and fixtures are used for this purpose (the apparatus of U.S. Pat. No. 4,055,900 being exemplary) less than optimum accuracy of measurement has resulted principally from a lack of means or method of compensating for deviation of visual axis from pupil center.

A patient's visual axes do not necessarily exit from the centers of respective pupils but may do so nasally or temporally to the extent of 0.1 to 0.2 mm for example. Accordingly, the techniques used heretofore of referencing from the center or other arbitrarily selected points on a patient's pupil fail to provide an assurance of whether spectacles frame measurements so taken accurately represent the true distances needed to ultimately properly locate a lens optical center relative to the patient's visual axis.

It is, accordingly, a principal object of this invention to provide novel means and method of assuring accurate alignment of lens optical center relative to a patient's visual axis in the case of each lens of a glazed spectacles frame intended to be worn by the patient.

A further object is to provide means and method for locating the position at which a patient's visual axis intersects the plane of a lens rim of a spectacles frame when the frame is properly fitted to the patient.

Other objects and advantages of the invention will become apparent from the following description.

SUMMARY OF THE INVENTION

The aforesaid objects and their corollaries are accomplished by providing in a spectacles frame fitting system, e.g. of the type represented in U.S. Pat. No. 4,055,900, a novel light-diffracting reticle located forwardly of a patient's pupil in the general plane of a lens rim of a spectacles frame when the frame, with attached fitting system, is placed in proper wearing position. The reticle, being in the form of a disc is of smaller diametral size than the patient's pupil and rendered manually vertically and horizontally adjustable in the plane of the lens rim.

With vertical and horizontal adjusting screws, the recticle is first roughly aligned with the patient's pupil, preferably by a fitting practitioner, and finally brought into precise alignment with the patient's visual axis by the patient himself.

This latter adjustment is accomplished by providing a distant bright spot target for the patient to monocularly fixate upon. The target is seen directly by virtue of the patient's free annular pupil aperture and a bright circular ring pattern is formed around the target by the presence of the diffracting disc.

If the bright ring pattern is not perceived as centered with the target, the patient is instructed to adjust the reticle to the extent necessary to bring the bright ring into an apparent concentric relationship with the target. This produces a centering of the reticle upon the patient's visual axis and distances from the so adjusted reticle to extreme lateral and extreme inferior points on the corresponding spectacles lens rim represent the measurements needed for finishing a lens to be mounted in the rim.

Details of the invention will become more readily apparent from the following description when taken in conjunction with the accompanying drawings in which.

DESCRIPTION OF THE PREFERRED EMBODIMENTS

Figure 1:
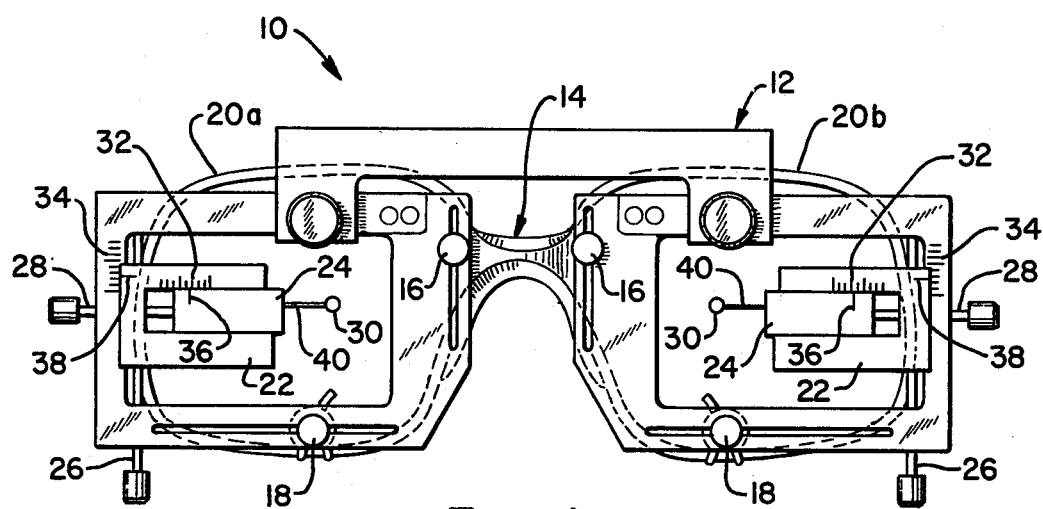
FIG. 1 is a front elevational view of a spectacles frame fitting system incorporating a preferred embodiment of the invention, the system is illustrated in a position of use upon a spectacles frame.

In FIG. 1 there is illustrated a measuring system 10 with which the position of intersection of a patient's visual axis with the plane of a spectacles lens rim may be precisely determined.

The system of FIG. 1 includes measuring device 12 and spectacles frame 14 to which the device 12 is attached. The attachment of device 12 to frame 14 is made by positioning locators 16 and 18 into the lens grooves of each of right and left eye lens rims 20a and 20b of frame 14. Locators 16 are positioned nasally of rims 20a and 20b at their extreme lateral extensions and locators 18 are positioned at the extreme inferior points of the lens grooves in rims 20a and 20b.

To the extent thus far described, measuring device 12 is generally similar to one of the embodiments of U.S. Pat. No. 4,055,900 and those interested in greater details of the aforementioned means and method of attaching device 12 to a spectacles frame may refer to U.S. Pat. No. 4,055,900.

Device 12 further incorporates vertically and horizontally adjustable sides 22 and 24 operable by vertically and horizontally disposed adjusting screws 26 and 28 respectively.

Extending laterally from each of horizontal slides 24 are reticles 30 from which the distances laterally and downwardly (horizontally and vertically) to extreme lateral and extreme inferior points in the grooves of each of lens rims may be measured with scales 32 and 34. Readings of scales 32 and 34 are taken from fiducial marks 36 and 38.

Measurements determined from scales 32 in each case represent the horizontal distance $d_1$ (FIG. 5) from the visual axis interecept and the optical center (OC) to extreme lateral edge of a lens L to be fitted in frame 14. Measurements taken from each of scales 34, on the other hand, represent the distance $d_2$ from the visual axis to the extreme inferior extension of the lens edge.

For example, in fitting a conventional single vision lens worn at 10° pantoscopic angle at normal fitting distance and where the objective is to cause the optical axis to intersect the center of rotation of the eye, the optical center is displaced downwardly 5 mm from the measurement on scale 34. When fitting special lenses, e.g. of the progressive addition type where the fitting objective is to obtain coincidence of primary gaze visual axis with optical center, the measurement on scale 34 is used unmodified.

Figure 5:
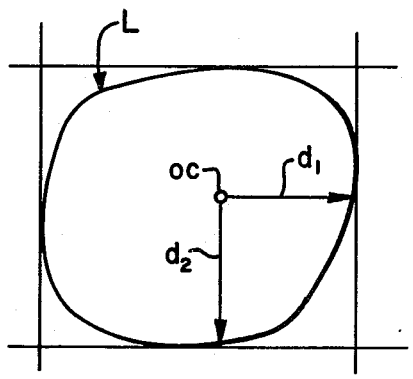
FIG. 5 diagrammatically illustrates the applicability of ophthalmic measurements obtained according to the invention.

It should be understood that while lens L of FIG. 5 is illustrated as being a patient's right eye lens, i.e. to be fitted in the right eye rim 20a of spectacles frame 14, similar measurements $d_1$ and $d_2$ would be used in mirror-image fashion for the finishing and glazing of a lens to be fitted into the left eye lens rim 20b of frame 14.

In the finishing of a lens L (FIG. 5) measurements $d_1$ and $d_2$ are utilized according to the traditional "boxing" method of specifying lens size. Those interested in these details may refer to U.S. Pat. No. 4,055,900 or to the publication referred to therein as "The Boxing Method of Specifying Eye Size" by Glen A. Frye, PhD. *Journal of the American Optometric Association*, February, 1959, pages 481–484.

Figure 2:
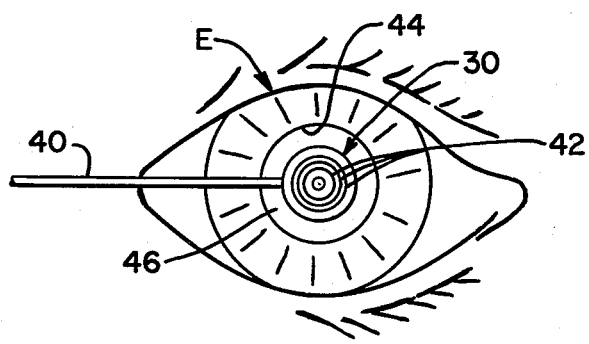
FIG. 2 is an enlarged fragmentary illustration of a reticle used in the system of FIG. 1, the reticle being shown in a position of use before a patient's eye.

Turning now to details of each reticle 30 and its use in establishing the location of intersection of a patient's visual axis with the plane of a lens rim 20a or 20b, there is depicted in FIG. 2 an enlarged illustration of one of reticles 30, namely that shown within the right eye lens rim 20a of frame 14. The reticle within lens rim 20b, being of identical construction and function, will not be separately described herein since the description which follows can be applied directly thereto.

Reticle 30 (FIG. 2) is suspended from slide 24 (FIG. 1) by support 40 which may comprise a length of wire. The reticle, being cemented or otherwise attached to wire 40, is preferably formed of a transparent or translucent glass or plastic material and is in the form of a thin disc rendered circularly light-diffracting by the provision of circular striations 42, ridges or other such means on at least one of its sides.

As depicted in FIG. 2, reticle 30 is of a diametral size less than that of a patient's pupil aperture 44 so that at maximum pupil contraction under ordinary examining or fitting room conditions, the placing of reticle 30 before the eye leaves a free annular pupil aperture 46.

Figure 3:
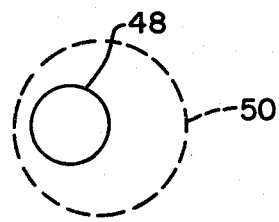
FIGS. 3 and 4 are diagrammatic illustrations of function of the apparatus and method of the invention.
Figure 4:
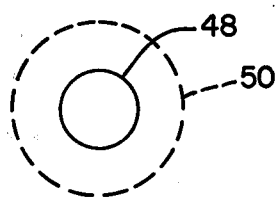

Alignment of reticle 30 with the visual axis of eye E (FIG. 2), for example, is accomplished by initially positioning the reticle forwardly of pupil aperture 44 using adjusting screws 26 and 28 of device 12. This initial adjustment of reticle 30 is preferably performed by the fitting practitioner and may be considered as a "coarse" adjustment since only positioning before the pupil aperture 44, but not necessarily in the illustrated centered relationship, is required. A bright spot target, e.g. a spot of light against a projection screen, is located forwardly of the patient and the patient is directed to fixate monocularly thereupon. The bright spot target is diagrammatically illustrated with the full line circle in each of FIGS. 3 and 4 and will be referred to hereinafter as target 48.

With reticle 30 before the pupil aperture 44, target 48 will be seen directly by virtue of the patient's free annular pupil aperture 46. Also seen will be a bright circular ring pattern of light around target 48 due to the presence of the diffracting reticle 30. This ring pattern is illustrated by broken lines 50 in FIGS. 3 and 4.

The patient is instructed to center the ring pattern around target 48 by self manipulation of adjusting screws 26 and 28. For example, if pattern 50 is off-center as in FIG. 3, the patient should bring it to the position illustrated in FIG. 4.

With pattern 50 viewed as being centered on target 48 (FIG. 4) reticle 30 can be considered as being centered upon the patient's visual axis. The reticle, in turn, being disposed in the plane of lens rim 20a gives indication of the position of intersection of the patient's visual axis with the plane of lens rim 20 and readings of scales 32 and 34 provide the aforementioned measurements $d_1$ and $d_2$ of FIG. 5.

Knowing measurements $d_1$ and $d_2$, lens L can be finished by edging to the shape and size required for fitting into lens rim 20a with its optical center OC approximately located relative to the patient's visual axis when the spectacles frame 14 with lens L is worn by the patient.

Those interested in details of the procedure used to finish ophthalmic lenses according to dimensions $d_1$ and $d_2$ may refer to U.S. Pat. No. 4,055,900.

It should be appreciated that various modifications and adaptations of the precise form of the invention here shown may be made to suit particular requirements. For example, means other than slides 22 and 24 may be used to adjustably support reticles 30 in the planes of lens rims 20a and 20b. The embodiments of FIGS. 1-4 of U.S. Pat. No. 4,055,900 are exemplary. Accordingly, it is intended that all modifications which incorporate the novel concept disclosed are to be construed as coming within the scope of the claims or the range of equivalency to which they are entitled in view of the prior art.

I claim:

1. Ophthalmic measuring apparatus attachable to a spectacles frame having a pair of lens rims and including means for supporting and adjusting an alignment reticle vertically and horizontally approximately in the plane of each of said lens rims wherein the improvement comprises, in each case of each reticle the structure of:
a circularly light diffracting disc of a diametral size less than that of the aperture of a person's pupil, said disc having circular striations for producing a perceivable bright ring pattern of light about an also perceivable bright spot target when such a target is located distantly of said disc and further when said disc is positioned before the person's pupil with fixation of the eye upon said target.

2. The measuring apparatus of claim 1 wherein said reticle supporting and adjusting means of said ophthalmic measuring apparatus includes vertically and horizontally adjustable slide means associated with each of said reticles and a wire support connecting each light-diffracting disc to one of said vertically and horizontally adjustable slide means.

3. The measuring apparatus of claim 2 including means for manually adjusting each of said slide means a scale and fiducial mark associated with each slide means, means for referencing extreme lateral and extreme inferior points on respective lens rims of said pair, said scales and fiducial marks indicating measurements of distances from said light diffracting discs to corresponding lateral and inferior points on said lens rims according to adjustment of said discs whereby measurement of position of a person's visual axis relative to said lateral and inferior points may be obtained as a result of said centering of said ring pattern of light causing a centering of said disc upon the corresponding visual axis of the person.

4. The method of locating the position at which one of a person's visual axes intersects the plane of one of the lens rims of a spectacles frame when the frame is properly fitted to the person, said method comprising the steps of:
- initially positioning a circularly light-diffracting disc approximately in said plane of said lens rim and before the pupil of a corresponding eye of said person, said disc being of smaller diametral size than the pupil aperture of the person thereby leaving an unobstructed annular pupil aperture about said disc;
- providing a bright spot target forwardly of said eye for fixation thereon by said person, said target being directly perceivable by the person by virtue of said annular pupil aperture together with a bright circular ring pattern therearound due to the presence of said disc;
- adjusting said disc vertically and laterally as needed for perception of centering of said ring pattern with said target to thereby effect a centering of said disc upon said visual axis whereby said arrived at position of said disc will represent the location of said position of intersection of said visual axis with said plane of said one lens rim.

5. The method according to claim 4 wherein said adjusting of said disc is performed by said person fitted to said frame.

6. A method according to claim 4 wherein said initial positioning of said disc before said eye is performed by a person other than said person fitted to said frame.

7. The method according to claim 6 wherein said adjusting of said disc is performed by said other person.

8. The method of claim 4 including the step of measuring the distances from said position of intersection of said visual axis within said plane of said lens rim to extreme lateral and extreme inferior points of a lens groove in said lens rim for use in the finishing of a lens to be glazed with its optical center properly located relative to said visual axis when worn in said spectacles frame.

* * * * *